United States Patent
Yamada et al.

(10) Patent No.: US 10,221,204 B2
(45) Date of Patent: Mar. 5, 2019

(54) PREPARATION METHOD FOR HIGH-PURITY 4'-GALACTOSYL-LACTOSE COMPOSITION

(71) Applicant: KABUSHIKI KAISHA YAKULT HONSHA, Minato-ku (JP)

(72) Inventors: Tetsuya Yamada, Minato-ku (JP); Hiroshi Hatano, Minato-ku (JP); Kazumasa Kimura, Minato-ku (JP); Hidetsugu Sotoya, Minato-ku (JP); Yoko Mori, Minato-ku (JP)

(73) Assignee: Kabushiki Kaisha Yakult Honsha, Minato-ku (JP)

( * ) Notice: Subject to any disclaimer, the term of this patent is extended or adjusted under 35 U.S.C. 154(b) by 0 days.

(21) Appl. No.: 15/308,037

(22) PCT Filed: Apr. 27, 2015

(86) PCT No.: PCT/JP2015/062673
§ 371 (c)(1),
(2) Date: Oct. 31, 2016

(87) PCT Pub. No.: WO2015/166903
PCT Pub. Date: Nov. 5, 2015

(65) Prior Publication Data
US 2017/0044200 A1    Feb. 16, 2017

(30) Foreign Application Priority Data
May 2, 2014 (JP) ................. 2014-095142

(51) Int. Cl.
*C07H 1/06*   (2006.01)
*C07H 3/06*   (2006.01)

(52) U.S. Cl.
CPC ............ *C07H 1/06* (2013.01); *C07H 3/06* (2013.01)

(58) Field of Classification Search
CPC ....................................................... C07H 1/06
See application file for complete search history.

(56) References Cited

U.S. PATENT DOCUMENTS

| 4,840,815 | A | 6/1989 | Meyer et al. |
| 4,942,054 | A | 7/1990 | Winter et al. |
| 4,973,489 | A | 11/1990 | Meyer et al. |
| 5,550,220 | A | 8/1996 | Meyer et al. |
| 2003/0186401 | A1* | 10/2003 | Shin .......... C12P 7/18 435/155 |
| 2011/0189342 | A1 | 8/2011 | Jeong et al. |

FOREIGN PATENT DOCUMENTS

| JP | 60-251896 A | 12/1985 |
| JP | S60251896 A | * 12/1985 |
| JP | 62-130695 A | 6/1987 |
| JP | 62-208293 A | 9/1987 |
| JP | 2-79992 A | 3/1990 |
| JP | 279992 A | * 3/1990 |
| JP | 4-500975 A | 2/1992 |
| JP | 6-55766 B2 | 7/1994 |
| JP | 7-89976 A | 4/1995 |
| JP | 2904687 B2 | 3/1999 |
| JP | 2003-325166 A | 11/2003 |
| WO | WO 90/13555 A1 | 11/1990 |
| WO | 2011/093907 A1 | 8/2011 |

OTHER PUBLICATIONS

Dombou et al, utilization of 4-B-Galactosyl-Lactose by Intestinal Bacteria, 1991, Denpun Kagaki, vol. 38, No. 4, pp. 365-367.*
Morales et al, Rapid Separation on Activated Charcoal of High Oligosaccharides in Honey, 2006, chromotagraphia, vol. 64, No. 3/4, pp. 233-238.*
English translation of JPS60251896A, 1985.*
English translation of JPH0279992A, 1990.*
Gorin et al, The structures of galatosyl-lactose and galactobiosyl-lactose produced from lactose by sporobolomyces singularis, 1963, canadian journal of chemistry, vol. 64 (Year: 1963).*
Torres, Galacto-oligosaccarides: production, properties, applications, and significance as prebiotics, 2010, comprehensive reviews in food science and food safety (Year: 2010).*
International Search Report dated Aug. 4, 2015 in PCT/JP2015/062673 filed Apr. 27, 2015.
Extended European Search Report dated Jan. 23, 2017 in Patent Application No. 15785433.2.

* cited by examiner

Primary Examiner — Melvin C. Mayes
Assistant Examiner — Stefanie Cohen
(74) Attorney, Agent, or Firm — Oblon, McClelland, Maier & Neustadt, L.L.P.

(57) ABSTRACT

A composition which has high 4'-GL purity and can be used as a reference standard for various analyses can be obtained by a more convenient method than one conventionally used. A method for preparing a high-purity 4'-GL composition includes the steps of: (A) subjecting a 4'-GL-containing galacto-oligosaccharide to activated carbon column chromatography, and performing stepwise elution with plural organic solvent aqueous solutions, wherein the organic solvent aqueous solutions are used such that the concentration of the organic solvent in the organic solvent aqueous solution is higher than the concentration of the organic solvent in the immediately preceding organic solvent aqueous solution with respect to a series of elutions; and (B) adding an organic solvent to the final fraction eluted in step (A), and crystallizing the 4'-GL.

4 Claims, No Drawings

PREPARATION METHOD FOR HIGH-PURITY 4'-GALACTOSYL-LACTOSE COMPOSITION

TECHNICAL FIELD

The present invention relates to a method of preparing a composition containing 4'-GL in high purity from a galacto-oligosaccharide containing 4'-GL (4'-galactosyl-lactose: Galβ1-4Galβ1-4Glc).

BACKGROUND ART

4'-GL is known as the main component of galacto-oligosaccharide that can promote proliferation of enteric Bifidobacteria. 4'-GL is also used as an index of galacto-oligosaccharide analysis.

Industrial production of 4'-GL-containing galacto-oligosaccharides utilizes a transfer reaction by β-galactosidase, using lactose as the feedstock. However, the purity of the galacto-oligosaccharide itself is typically low when purification step and the like are not performed.

As a technique that improves purity through purification of oligosaccharide, PTL 1 discloses a glucosamino oligosaccharide purification method in which a polymer prepared by introducing a carboxylmethyl group to a polymer having a hydroxyl group is used as a chromatography filler. However, there is no report of a method that is intended to improve the purity of components of galacto-oligosaccharide, particularly 4'-GL, through purification of galacto-oligosaccharide. Even compositions available as a reference standard of 4'-GL are not sufficient in purity.

CITATION LIST

Patent Literature

PTL 1: JP-B-6-55766

SUMMARY OF INVENTION

Technical Problem

It is accordingly an object of the present invention to provide a method of conveniently and inexpensively preparing a composition that has high 4'-GL purity and that can be used as a reference standard for various analyses.

Solution to Problem

The present inventors conducted extensive studies to solve the foregoing problems, and found that a composition having high 4'-GL purity can be obtained by combining stepwise elution using an organic solvent with crystallization. The present invention was completed on the basis of this finding.

Specifically, the present invention is a method for preparing a high-purity 4'-GL composition, the method including the steps of:

(A) subjecting a 4'-GL-containing galacto-oligosaccharide to activated carbon column chromatography, and performing stepwise elution with plural organic solvent aqueous solutions, wherein the organic solvent aqueous solutions are used such that the concentration of the organic solvent in the organic solvent aqueous solution is higher than the concentration of the organic solvent in the immediately preceding organic solvent aqueous solution with respect to a series of elutions; and (B) adding an organic solvent to the final fraction eluted in step (A), and crystallizing the 4'-GL.

The present invention is a high-purity 4-GL composition obtained by using the foregoing preparation method.

Advantageous Effects of Invention

The method for preparing a high-purity 4'-GL composition of the present invention is a method in which stepwise elution using an organic solvent is combined with crystallization, whereby a composition containing 4'-GL in high purity can be conveniently and inexpensively prepared from a galacto-oligosaccharide containing 4'-GL.

The high-purity 4'-GL composition obtained by using the method for preparing a high-purity 4'-GL composition of the present invention can be used as a reference standard for various analyses.

DESCRIPTION OF EMBODIMENTS

Step (A) in the method for preparing a high-purity 4'-GL composition of the present invention (hereinafter, referred to as "preparation method of the present invention") is a step in which a 4'-GL-containing galacto-oligosaccharide is subjected to activated carbon column chromatography, and in which stepwise elution is performed with plural organic solvent aqueous solutions, wherein the organic solvent aqueous solutions are used such that the concentration of the organic solvent in the organic solvent aqueous solution is higher than the concentration of the organic solvent in the immediately preceding organic solvent aqueous solution with respect to a series of elutions.

The 4'-GL-containing galacto-oligosaccharide is not particularly limited, as long as it is a galacto-oligosaccharide containing 4'-GL. Examples of such galacto-oligosaccharides include a galacto-oligosaccharide produced by using a transfer reaction by β-galactosidase.

Specifically, for the production of 4'-GL-containing galacto-oligosaccharides using a transfer reaction by β-galactosidase, lactose may be acted upon by β-galactosidase, or by microorganisms that produce β-galactosidase. Preferably, lactose may be acted upon by a combination of β-galactosidase and a sugar-utilizing microorganism to increase the proportion of trisaccharides in the galacto-oligosaccharides.

Examples of the β-galactosidase producing microorganisms include microorganisms of the genus *Kluyveromyces*, such as *Kluyveromyces lactis*, and microorganisms of the genus *Sporobolomyces*, such as *Sporobolomyces singularis*. Other examples include *Streptococcus thermophilus, Lactobacillus bulgaricus, Streptococcus lactis, Lactobacillus salivarius, Lactobacillus leichmannii, Lactobacillus helveticus, Bacillus brevis, Bacillus stearothermophilus, Bifidobacterium bifidum, Bifidobacterium breve, Bifidobacterium longum,* and *Bifidobacterium adolescentis*. Preferred are microorganisms of the genus *Sporobolomyces*, more preferably *Sporobolomyces singularis*, particularly preferably the *Sporobolomyces singularis* ISK-##2B6 previously reported by the applicant of this patent application. The *Sporobolomyces singularis* ISK-##2B6 has been deposited by the present applicant as FERM P-18817 at The National Institute of Advanced Industrial Science and Technology, The International Patent Organism Depositary (Tsukuba Center, Chuou Dairoku, 1-1-1, Higashi, Tsukuba-shi, Ibaraki, 305-8566) as of Apr. 10, 2002. (Of note, as of Apr. 1, 2013, The International Patent Organism Depositary has been renamed as The National Institute of Technology and Evaluation, International Patent Organism Depositary, and relocated to 120, 5-8, 2-chome, Kazusa-Kamatari, Kisarazu, Chiba, 292-0818.) The *Sporobolomyces singularis* JCM5356, a parental strain of the *Sporobolomyces singularis* ISK-##2B6, also may preferably be used as *Sporobolomyces singularis*. This strain is available for a fee from Riken BRC (3-1-1, Koyadai, Tsukuba, Ibaraki, Japan, 305-0074). These microorganisms may be used either alone or in a combination of two or more.

Examples of the sugar-utilizing microorganisms include *Saccharomyces cerevisiae* and *Saccharomyces unisporus*, typical bread yeasts available in the market. These microorganisms may be used either alone or in a combination of two or more. The sugars utilized by the sugar-utilizing microorganisms are not particularly limited. However, the microorganisms are preferably one that utilizes glucose, in order to increase the proportion of trisaccharides in the galacto-oligosaccharides.

Production of 4'-GL-containing galacto-oligosaccharides through the use of microorganisms such as above is not limited to particular conditions. For example, a β-galactosidase producing microorganism, and, optionally, a sugar-utilizing microorganism are added to a heated solution (about 40° C.) of lactose in water, and the mixture is cultured for about 1 day while being stirred. The amount of β-galactosidase producing microorganism added is not particularly limited. For example, the microorganism may be added to make the β-galactosidase activity 100 to 600 U per kilogram of lactose. The amount of sugar-utilizing microorganism added is not particularly limited either. For example, the microorganism may be added to in an amount of 0.0001 to 10 mass % ($1\times10^7$ to $1\times10^{12}$ cfu) in terms of a dry powder of the microorganism per kilogram of lactose. β-Galactosidase activity is measured in the manner described in the Production Examples below. The reaction that generates galacto-oligosaccharides may be quenched by, for example, heating the reaction mixture to about 85° C., and maintaining the temperature for about 10 minutes. Preferably, the cells are removed by centrifugation or filtration after the reaction.

Activated carbon column chromatography may be performed by charging the 4'-GL-containing galacto-oligosaccharides into a column charged with activated carbon, and performing stepwise elution using an organic solvent aqueous solution.

The type of the activated carbon charged into the column is not particularly limited, and the activated carbon may be, for example, in the form of a powder or a granule, or in a crushed state. The method for charging the activated carbon into the column is not particularly limited either. For example, the activated carbon may be added to water, and charged into the column in the form of a slurry, and allowed to stand in the column. The amount of activated carbon charged into the column is not particularly limited, and is, for example, ⅓ to ¼ of the volume of the column used. The material of the column is not particularly limited, and may be, for example, glass or plastic. The column diameter and height are not particularly limited, and the column may have a diameter of, for example, 2 to 15 cm, and a height of, for example, 30 to 100 cm.

The stepwise elution using an organic solvent is performed such that the concentration of the organic solvent in the organic solvent aqueous solution is higher than the concentration of the organic solvent in the immediately preceding organic solvent aqueous solution with respect to a series of elutions. Specifically, the elution process begins with washing the activated carbon column by passing water. Thereafter, an organic solvent aqueous solution is passed through the column, followed by passage of another organic solvent aqueous solution having a higher concentration of organic solvent than the organic solvent concentration of the preceding elution. The term "stepwise elution" is used to refer to such a procedure where an organic solvent aqueous solution of a different concentration is passed through the activated carbon column at least twice. Preferably, an organic solvent aqueous solution is passed two times. The amount of the organic solvent aqueous solution used for single elution (passage) is not particularly limited, and is, for example, 2 to 6 times the volume of the activated carbon used. The rate of stepwise elution is not particularly limited either, and is, for example, such a rate that the liquid level of the eluate moves at 2 to 6 cm/min.

The organic solvent used in step (A) is not particularly limited, and is preferably an organic solvent having polarity, more preferably an alcohol of 1 to 3 carbon atoms, particularly preferably methanol. The concentration of the organic solvent is preferably 5 to 40 mass % (hereinafter, simply "%"), particularly preferably 10 to 30%.

Specifically, the stepwise elution using an organic solvent aqueous solution is performed first with an organic solvent aqueous solution having an organic solvent concentration of 5 to 25%, and then with an organic solvent aqueous solution having an organic solvent concentration of 10 to 40%, more preferably first with an organic solvent aqueous solution having an organic solvent concentration of 10 to 20%, and then with an organic solvent aqueous solution having an organic solvent concentration of 15 to 30%, particularly preferably first with an organic solvent aqueous solution having an organic solvent concentration of 15 to 20%, and then with an organic solvent aqueous solution having an organic solvent concentration of 20 to 30%.

Concentration and dilution processes such as by filtration, centrifugation, or reducing pressure may be performed during the elution procedure. The final fraction eluted in step (A) may be used either directly, or preferably used after drying the solid component through concentration.

The trisaccharides contained in the galacto-oligosaccharides are specifically eluted after the step (A) described above. The proportion of trisaccharides in the galacto-oligosaccharides may be measured by using the method described in the Production Examples below.

The step (B) of the preparation method of the present invention is a step of adding an organic solvent to the final fraction eluted in step (A), and crystallizing the 4'-GL.

The organic solvent used in the step (B) is not particularly limited, and is preferably an organic solvent that is miscible with water. The organic solvent that is miscible with water is preferably at least one selected from methanol, acetone, and ethanol, and is particularly preferably methanol. The amount of organic solvent added is not particularly limited, and is, for example, 10 to 30 times the content (volume) of water in the fraction used for crystallization. The concentration of the organic solvent to be added is not particularly limited, and is preferably about 100%.

The crystallization of 4'-GL is performed, for example, by adding an organic solvent to the final fraction eluted in step (A), and allowing the solution to stand. For crystallization, for example, ultrasonic waves may be applied for easy precipitation of crystals, before allowing the solution to stand.

In the step (B) described above, only the trisaccharides crystallize, and other sugars (including monosaccharides, disaccharides, and tetrasaccharides) do not crystallize. Isomers such as 4'-GL and Galβ1-4Galβ1-3Glc are present in the trisaccharide sugars in the galacto-oligosaccharides, and 4'-GL is crystallized in larger proportions than other trisaccharide isomers in step (B). This increases the proportion (purity) of 4'-GL in the trisaccharide isomers. The proportion of 4'-GL in the trisaccharide isomers can be measured by using the method described in the Examples below.

After step (B), the crystallized high-purity 4'-GL composition may be subjected to post processes, including washing with the same organic solvent used for the crystallization, and drying.

The composition obtained by using the preparation method of the present invention is a composition containing 4'-GL in high purity, specifically 90% or more, preferably 94% or more, more preferably 95% or more in terms of the content of 4'-GL in the trisaccharide isomers contained in the composition. The high-purity 4'-GL composition obtained by using the preparation method of the present invention has a solid content of 95% or more, and sugars other than trisaccharide isomers (including monosaccharides, disaccharides, and tetrasaccharides) do not crystallize in the crystallization step. Because the trisaccharide isomers account for all the solid component of the composition, the 4'-GL content in the composition can be determined as the product of "the solid content of the composition and the proportion of 4'-GL in the trisaccharide isomers." The composition contains 4'-GL in an amount of 88% or more, preferably 90% or more, more preferably 92% or more, further preferably 95% or more.

The high-purity 4'-GL composition obtained in the manner described above can be used, for example, as a reference standard for various analyses, or as a raw material of products such as food and beverages, and drugs.

EXAMPLES

The present invention is described below in greater detail referring to Production Examples and Examples. The present invention, however, is in no way limited by these examples.

Production Example 1

Preparation of Sugar Solution

Two kilograms of lactose was dissolved in 2.7 kg of hot water having a temperature of 80° C. The mixture was cooled to 40° C., and the temperature was maintained in a thermostat bath. To the mixture were then added 157 g of a cell solution of *Sporobolomyces singularis* YIT10047 (ISK-##2B6; FERM P-18817; β-galactosidase activity: 4,000 U/kg), and 63 g of *Saccharomyces cerevisiae* (available from Oriental Yeast Co., Ltd.: Regular Yeast; 6.3×10$^{11}$ cfu). These were allowed to react for 22 h at the maintained temperature of 40° C. while being stirred. The reaction was quenched after raising the temperature to 85° C., and maintaining the temperature for 10 min. After the reaction, the reaction mixture was centrifuged (12,000× g, 30 min), and the cells used for the reaction were removed to obtain a sugar solution. The sugar solution (product) was analyzed by size exclusion HPLC under the conditions below, and a composition analysis based on sugar chain length was performed using the area percentage. The results are shown in Table 1.

Measurement of β-Galactosidase Activity in Cell Solution of *Sporobolomyces singularis*

The β-galactosidase activity (U) of the cell solution of *Sporobolomyces singularis* YIT10047 (ISK-##2B6; FERM P-18817) was measured by using the same method as the measuring method described in WO2012/141244.

HPLC Conditions
  Apparatus: Shimadzu Prominence UFLC
  Column: SUGAR KS-802 (8.0 φ×300 mm; Showa Denko)
  Column temperature: 80° C.
  Injection amount: 10 μL
  Mobile phase: purified water
  Analysis time: 30 min
  Flow rate: 0.5 mL/min
  Detection: differential refractive index

TABLE 1

|  | Product | Oligomate 55N*[1] |
|---|---|---|
| Tetrasaccharides and higher | 7.0% | 7.1% |
| Trisaccharides | 65.6% | 34.4% |
| Disaccharides | 26.7% | 27.5% |
| Monosaccharides | 0.7% | 31% |

*[1]Galacto-oligosaccharide manufactured by Yakult Pharmaceutical Industry Co., Ltd, produced from lactose acted upon by a cell solution of Sporobolomyces singularis, and β-galactosidase derived from Kluyveromyces lactis.

From these results, it was found that the trisaccharide content increases when *Sporobolomyces singularis* and sugar-utilizing *Saccharomyces cerevisiae* are used in combination, as compared to the commercially available galacto-oligosaccharide product obtained by reaction with *Sporobolomyces singularis*, and *Kluyveromyces lactis*-Derived β-galactosidase.

Example 1

Assessment of Elution Conditions (1)

The sugar solution prepared in Production Example 1 was concentrated with an evaporator to obtain a concentrated sugar solution with a Bx of 72.3. A 1.3-g portion of the concentrated sugar solution was diluted with water to make a 25-mL dilute sugar solution. The dilute sugar solution was then loaded into open column chromatography (column diameter: 2 cm, height: 30 cm) that had been charged with 25 mL of activated carbon (activated carbon for chromatography, manufactured by Wako Pure Chemical Industries, Ltd.) using an ordinary method. The dilute sugar solution-loaded column was washed with purified water, and the sugar was eluted by performing single elution or stepwise elution as shown in the Table 2 below. The solvent was used in an amount of 100 mL in each elution. Each stage of washing and elution took about 10 min. The washing and elution were performed at such a rate that the liquid levels of purified water and the eluate lowered at 5 cm/min.

The eluate obtained after the first elution in the single elution, and the eluate obtained after the second elution in the stepwise elution in Table 2 were collected, and concentrated with an evaporator under reduced pressure. The resulting eluate was adjusted to an appropriate concentration, and passed through a 0.45-μm filter. The filtrate was analyzed by size exclusion HPLC under the same conditions used in Production Example 1, and a composition analysis based on sugar chain length was performed for each eluate using the area percentage. The proportion of trisaccharides in all sugars was then determined from the result of the composition analysis based on sugar chain length. The results are shown in Table 2.

TABLE 2

|  | Washing | First elution | Second elution | Proportion of trisaccharides in all sugars |
|---|---|---|---|---|
| Single elution | Purified water | 20% Methanol solution | None | 70.59% |
| Stepwise elution 1 | Purified water | 15% Methanol solution | 20% Methanol solution | 95.72% |

As can be seen from these results, the stepwise elution specifically eluted trisaccharides.

Example 2

Assessment of Elution Conditions (2)

The sugar was eluted in the same manner as in the stepwise elution 1 of Example 1, except that the concentration of the methanol aqueous solution was varied as shown in Table 3. The proportion of trisaccharides in all sugars was also determined in the same manner as in Example 1. The results are shown in Table 3.

TABLE 3

|  | Washing | First elution | Second elution | Proportion of trisaccharides in all sugars |
|---|---|---|---|---|
| Stepwise elution 2 | Purified water | 5% Methanol solution | 10% Methanol solution | 83.07% |
| Stepwise elution 3 | Purified water | 10% Methanol solution | 15% Methanol solution | 94.06% |
| Stepwise elution 1 | Purified water | 15% Methanol solution | 20% Methanol solution | 95.72% |
| Stepwise elution 4 | Purified water | 20% Methanol solution | 30% Methanol solution | 95.47% |
| Stepwise elution 5 | Purified water | 25% Methanol solution | 40% Methanol solution | 86.24% |

From these results, it was found that the proportion of trisaccharides in the eluate after the second elution becomes 80% or more when the methanol aqueous solution used for the first elution has a methanol concentration of 5 to 25%, and the methanol aqueous solution used for the second elution has a methanol concentration of 10 to 40%. Particularly, it was found that the proportion of trisaccharides in the eluate after the second elution becomes 90% or more when the methanol aqueous solution used for the first elution has a methanol concentration of 10 to 20%, and the methanol aqueous solution used for the second elution has a methanol concentration of to 30%. It was also found that the proportion of trisaccharides in the eluate after the second elution becomes even higher, 95% or more, when the methanol aqueous solution used for the first elution has a methanol concentration of 15 to 20%, and the methanol aqueous solution used for the second elution has a methanol concentration of 20 to 30%.

Example 3

Assessment of Crystallization Conditions (1)

The sugar solution prepared in the same manner as in Production Example 1 was concentrated with an evaporator under reduced pressure to obtain a concentrated sugar solution with a Bx of 72.3. A 22.1-g portion of the concentrated sugar solution was diluted with purified water to make a 400-mL dilute sugar solution. The dilute sugar solution was then loaded into open column chromatography (column diameter: 6 cm, height: 40 cm) that had been charged with 400 mL of activated carbon (activated carbon for chromatography, manufactured by Wako Pure Chemical Industries, Ltd.) using an ordinary method. The dilute sugar solution-loaded column was washed with purified water, and the sugar was eluted in the same manner as in the stepwise elution 1 of Example 1, using a 15% methanol aqueous solution, and a 20% methanol aqueous solution, in this order. The solvent was used in an amount of 1,600 mL in each elution. The eluate obtained after the elution was concentrated with an evaporator under reduced pressure, and dried in a desiccator under reduced pressure to obtain 2.3 g of a concentrate (solid content of 2.3 g).

The concentrate was dissolved in 2.5 mL of purified water. Thereafter, 50 mL of methanol was added to the solution in small portions while stirring the mixture until the final methanol concentration reached 95.2% (v/v). The mixture was then placed under ultrasonic waves to promote crystal formation, and was allowed to stand overnight at room temperature. The generated crystals were filtered with a filter-equipped funnel, and the crystals were washed with methanol, and dried in a desiccator. In order to confirm changes in the concentration of 4'-GL in the trisaccharide isomers after crystallization, the trisaccharide isomers containing 4'-GL were quantified using the method below, and the proportion of 4'-GL in the trisaccharide isomers was determined. The proportions of trisaccharide isomers other than 4'-GL were also determined. The proportion of 4'-GL in the trisaccharide isomers of the concentrate, and the proportions of trisaccharide isomers other than 4'-GL were also determined before crystallization in the same manner. The results are shown in Table 4.

4'-GL Quantification Method

About 5 mg of a sample was placed in a threaded test tube, and concentrated with an evaporator under reduced pressure. After concentration, the sample was dried in a desiccator under reduced pressure. Thereafter, 200 μL of an acetic acid solution containing about 50 equivalents of 2-aminopyridine was added to the solid sample, and these were reacted in a heat reaction performed at 90° C. for 1 h. To the reaction mixture was then added 250 μL of a borane-dimethylamine reagent prepared in a concentration of 195 mg/mL (acetic acid), and the sugar was reduced at 80° C. for 50 min to obtain a pyridylaminated derivative. The pyridylaminated derivative was transferred to a 50-mL Falcon tube, and diluted to about 25 mL with purified water. A 1 M sodium hydroxide aqueous solution was then added to the diluted solution to make the pH weakly acidic to neutral. This was followed by dialysis using a MicroAcilyzer S1 (manufactured by Asahi Kasei). Dialysis was performed with a dialysis membrane AC-120-10 (manufactured by Astom), and a 0.5% sodium nitrate aqueous solution used as electrode solution. The end point was set at 0 A. The processed liquid was concentrated with an evaporator under reduced pressure, and dried with a desiccator under reduced pressure. The sample was dissolved in purified water, and the filtrate through a 0.45-μm filter was analyzed by HPLC. Because pyridylaminated reagent residues were observed, the proportion of 4'-GL in the trisaccharide isomers was determined from the percentage of the peak area detected after 22 minutes from the start of analysis. The proportions of trisaccharide isomers other than 4'-GL were also determined.

A peak for 4'-GL occurred after 26.8 minutes from the start of analysis, whereas a peak for Galβ1-4Galβ1-3Glc occurred after 41.2 minutes from the start of analysis.

HPLC Conditions

Apparatus: Shimadzu Prominence UFLC
Column: PEGASIL ODS SP300 (4.6 mm φ×250 mm; manufactured by Senshu Scientific Co., Ltd.)
Column temperature: 25° C.
Injection amount: 10 μL
Mobile phase: 0.2 M sodium citrate buffer (pH 5.7)
Analysis time: 70 min
Flow rate: 0.5 mL/min
Detection: UV (310 nm)

TABLE 4

| Isomers of trisaccharides | Before crystallization | After crystallization |
|---|---|---|
| Galβ1-4Galβ1-4Glc (4'-GL) | 90.0% | 95.8% |
| Galβ1-4Galβ1-3Glc | 6.8% | 1.7% |
| Other | 3.2% | 2.5% |

From these results, it was found that the purity of 4'-GL in the trisaccharide isomers can improve after the crystallization with methanol. The product crystals were at least 95% solid, and sugars other than trisaccharide isomers did not crystallize in the crystallization step. Because the trisaccharide isomers account for all the solid component of the crystals, the proportion of 4'-GL in the composition is 91% or more (=95%×95.8%).

Example 4

Assessment of Crystallization Conditions (2)

The sugar solution prepared in the same manner as in Production Example 1 was concentrated with an evaporator under reduced pressure to obtain a concentrated sugar solution with a Bx of 72.3. A 120-g portion of the concentrated sugar solution was diluted with purified water to make a 2,000-mL dilute sugar solution. The dilute sugar solution was then loaded into open column chromatography (column diameter: 9 cm, height: 80 cm) that had been charged with 2,000 mL of activated carbon (activated carbon for chromatography, manufactured by Wako Pure Chemical Industries, Ltd.) using an ordinary method. The dilute sugar solution-loaded column was washed with purified water, and the sugar was eluted in the same manner as in the stepwise elution 1 of Example 1, using a 15% methanol aqueous solution, and a 20% methanol aqueous solution, in this order. The solvent was used in an amount of 8,000 mL in each elution. The eluate obtained after the elution was concentrated with an evaporator under reduced pressure, and dried in a desiccator under reduced pressure to obtain 12.5 g of a concentrate (solid content of 12.5 g).

The concentrate was dissolved in 12.5 mL of purified water, and separated into 2.5-mL portions. Thereafter, 50 mL of acetone or ethanol—a solvent that is miscible with water—was added in small portions to the concentrate solution until the final concentration reached 95.2% (v/v). The mixture was then placed under ultrasonic waves to promote crystal formation, and was allowed to stand overnight at room temperature. The generated crystals were filtered with a filter-equipped funnel, and the crystals were washed with the same organic solvent used for the crystallization, and dried in a desiccator. In order to confirm changes in the concentration of 4'-GL in the trisaccharide isomers after crystallization, the trisaccharide isomers containing 4'-GL were quantified in the same manner as in Example 3, and the proportion of 4'-GL in the trisaccharide isomers was determined. The results are shown in Table 5. Table 5 also shows the proportion of 4'-GL in the trisaccharide isomers after the crystallization with methanol performed in Example 3.

TABLE 5

| Crystallization solvent | Proportion of 4'-GL in trisaccharide isomers before crystallization | Proportion of 4'-GL in trisaccharide isomers after crystallization |
|---|---|---|
| Acetone | 90.0% | 94.4% |
| Ethanol | 90.0% | 94.4% |
| Methanol | 90.0% | 95.8% |

From these results, it was found that the purity of 4'-GL in the trisaccharide isomers can improve after the crystallization with acetone or ethanol, as with the case of methanol. However, the proportion of 4'-GL in the trisaccharide isomers after the crystallization was the highest when methanol was used. As with the case of methanol, the product crystals were at least 95% solid, and sugars other than the trisaccharide isomers did not crystallize in the crystallization step with acetone or methanol. Because the trisaccharide isomers account for all the solid component of the crystals, the proportion of 4'-GL in the composition is 89.6% or more (=95%×94.4%).

Example 5

Assessment with Other Strains

A sugar solution was prepared in the same manner as in Production Example 1, stepwise elution was performed under the same conditions used for the stepwise elution 1 of Example 1, and 4'-GL was crystallized under the same conditions used in Example 3, except that the cell solution of *Sporobolomyces singularis* YIT10047 (ISK-##2B6) was replaced with a cell solution of *Sporobolomyces singularis* JCM5356. This cell solution was used in an amount that yields the same level of β-galactosidase activity as that produced with the amount of the *Sporobolomyces singularis* YIT10047 solution used in Production Example 1. As a result, the proportion of 4'-GL in the trisaccharides was 95% or more in the crystals produced. The crystals were at least 95% solid, and sugars other than the trisaccharide isomers did not crystallize in the crystallization step. Because the trisaccharide isomers account for all the solid component of the crystals, the proportion of 4'-GL in the composition is 90.3% or more (=95%×95%).

INDUSTRIAL APPLICABILITY

The method for preparing a high-purity 4'-GL composition of the present invention provides a way to conveniently obtain a high-purity 4'-GL composition. The high-purity 4'-GL composition obtained by using the preparation method can be used as a reference standard for various analyses, or as a raw material of products such food and beverages, and drugs.

The invention claimed is:

1. A method for preparing a high-purity 4'-galactosyllactose (4'-GL) composition comprising 92 mass % or more of 4'-GL, the method comprising:

(A) subjecting a 4'-GL-containing galacto-oligosaccharide to activated carbon column chromatography, and performing stepwise elution with a 10-20 mass % methanol solution and then with a 15-30 mass % methanol solution, wherein the methanol solutions are used such that a concentration of methanol in one methanol solution is higher than a concentration of methanol in an immediately preceding methanol solution, thereby producing a final fraction; and (B) adding at least one organic solvent selected from the group consisting of methanol, acetone and ethanol to the final fraction and crystallizing the 4'-GL, thereby producing the high-purity 4'-galactosyl-lactose (4'-GL) composition comprising 92 mass % or more of 4'-GL, wherein the 4'-GL-containing galacto-oligosaccharide used in said subjecting (A) is one generated using *Sporobolomyces singularis* and *Saccharomyces cerevisiae*.

2. The method according to claim 1,
wherein the high-purity 4'-GL composition comprises not less than 95 mass % of 4'-GL.

3. The method according to claim 1,
wherein the at least one organic solvent is methanol.

4. The method according to claim 1,
wherein the final fraction contain 80.0 mass % or more of 4'-GL.

* * * * *